United States Patent
Chu et al.

(10) Patent No.: US 11,981,925 B2
(45) Date of Patent: May 14, 2024

(54) DECIDUAL PLACENTAL MESENCHYMAL STEM CELL AND THE USE OF THE CELL FOR PREPARING PHARMACEUTICAL COMPOSITIONS FOR PROMOTING ANGIOGENESIS

(71) Applicant: Biospring Medical Co., Ltd., New Taipei (TW)

(72) Inventors: Li-Li Chu, New Taipei (TW); Meng-Shiue Wu, New Taipei (TW)

(73) Assignee: BIOSPRING MEDICAL CO., LTD., New Taipei (TW)

( * ) Notice: Subject to any disclaimer, the term of this patent is extended or adjusted under 35 U.S.C. 154(b) by 0 days.

(21) Appl. No.: 17/539,253

(22) Filed: Dec. 1, 2021

(65) Prior Publication Data
US 2023/0101074 A1    Mar. 30, 2023

(30) Foreign Application Priority Data
Sep. 27, 2021 (WO) ................ PCT/CN2021/120946

(51) Int. Cl.
*C12N 5/0775* (2010.01)
*A61K 35/28* (2015.01)

(52) U.S. Cl.
CPC ............ *C12N 5/0668* (2013.01); *A61K 35/28* (2013.01); *C12N 2500/90* (2013.01); *C12N 2501/24* (2013.01); *C12N 2501/25* (2013.01)

(58) Field of Classification Search
CPC .............. C12N 5/0668; C12N 2501/24; C12N 2501/25
See application file for complete search history.

(56) References Cited

U.S. PATENT DOCUMENTS

2020/0131481 A1* 4/2020 Abraham ................ C12M 21/00

FOREIGN PATENT DOCUMENTS

TW            201313901 A        4/2013

OTHER PUBLICATIONS

Huang et al (An efficient protocol to generate placental chorionic plate-derived mesenchymal stem cells with superior proliferative and immunomodulatory properties. Stem Cell Res and Therapy, vol. 10, Oct. 2019). (Year: 2019).*
Schmidt et al (Only humans have human placentas: molecular differences between mice and humans. J of Rep Immuno, vol. 108, Apr. 2015) (Year: 2015).*
Liang et al (De novo generation of macrophage from placenta-derived hemogenic endothelium. Dev Cell, vol. 56, Jul. 2021) (Year: 2021).*
Zhang et al (Cytokines, Inflammation and Pain. Int Anesthesiol Clin, vol. 45, 2007 (Year: 2007).*
Hu et al (TNF-α and IFN-γ synergistically inhibit the repairing ability of mesenchymal stem cells on mice colitis and colon cancer. Am J Transl Res, vol. 11, Sep. 2019) (Year: 2019).*
Su et al (Fluorescent nanodiamonds enable quantitative tracking of human mesenchymal stem cells in miniature pigs. Sci Rep, vol. 7, Mar. 2017 (Year: 2017).*
Chapter 7: Placenta and Extraembryonic Membranes, Bruce Carlson, Human Embryology and Developmental Biology, 5th edition, 2014 (Year: 2014).*
Castrechini et al (Decidua Parietalis-Derived Mesenchymal Stromal Cells Reside in a Vascular Niche Within the Choriodecidua. Reproductive sciences, vol. 19, 2012 (Year: 2012).*
Siakavellas et al (Decoy receptor 3: Its role as biomarker for chronic inflammatory diseases. World J Immunol, vol. 3, 2013 (Year: 2013).*
Hayashi et al (Decoy Receptor 3 Expressed in Rheumatoid Synovial Fibroblasts Protects the Cells Against Fas-Induced Apoptosis. Arthritis & Rheumatism, vol. 56, 2007 (Year: 2007).*
Kim et al (Increased expression of soluble decoy receptor 3 in acutely inflamed intestinal epithelia. Clinical Immunology, vol. 115, 2005 (Year: 2005).*
Funke et al (Functional characterization of decoy receptor 3 in Crohn's disease. Gut, 2009). (Year: 2009).*
Su L. J. et al., Fluorescent nanodiamonds enable quantitative tracking of human mesenchymal stem cells in miniature bigs. Sci Rep. Mar. 30, 2017;7:45607.
Brennan M. A. et al., Biomaterials functionalized with MSC secreted extracellular vesicles and soluble factors for tissue regeneration. Adv Funct Mater. Sep. 10, 2020;30(37):1909125.
Kim S. et al., Selective Induction of Tumor Necrosis Receptor Factor 6/Decoy Receptor 3 Release by Bacterial Antigens in Human Monocytes and Myeloid Dendritic Cells, Infection and Immunity, Jan. 2004, p. 89-93.

* cited by examiner

*Primary Examiner* — Valarie E Bertoglio
*Assistant Examiner* — Matasha Dhar
(74) *Attorney, Agent, or Firm* — Hannah Tien

(57) ABSTRACT

Human decidual placental mesenchymal stem cell having an increased expression level of decoy receptor 3 (DcR3), and a method for obtaining the human decidual placental mesenchymal stem cells having an increased expression level of DcR3 are provided, wherein human decidual placental mesenchymal stem cells are cultured in a culture dish containing a serum-free medium and the DcR3 expression of the human decidual placental mesenchymal stem cells are increased by stimulation of at least one inflammatory cytokine for 48 hours, and obtaining the human decidual placental mesenchymal stem cells having an increased expression level of DcR3, wherein the increased expression level of DcR3 is significantly higher than that of human decidual placental mesenchymal stem cells with the stimulation is higher than that of human decidual placental mesenchymal stem cells cultured without the stimulation of the at least one inflammatory cytokine.

6 Claims, 11 Drawing Sheets
(5 of 11 Drawing Sheet(s) Filed in Color)

Prior art

Prior art

Prior art

Prior art

DECIDUAL PLACENTAL MESENCHYMAL STEM CELL AND THE USE OF THE CELL FOR PREPARING PHARMACEUTICAL COMPOSITIONS FOR PROMOTING ANGIOGENESIS

CROSS-REFERENCES TO RELATED APPLICATION

This application claims priority to International Application No. PCT/CN2021/120946 filed Sep. 27, 2021, which is hereby incorporated by reference in its entirety.

FIELD OF THE INVENTION

The present invention is related to decidual placental mesenchymal stem cells (pcMSCs) having increased expression level of decoy receptor 3 DcR3) and its culturing method, in particular, an induction step is added to currently existing mesenchymal stem cell culturing method, so that the expression of Decoy receptor 3 (DcR3) is highly expressed in the decidual placental mesenchymal stem cells (pcMSCs). The present invention is further related to a use of decidual placental mesenchymal stem cells (pcMSCs) for preparing pharmaceutical compositions for promoting angiogenesis.

BACKGROUND OF THE INVENTION

In the present, the biomarkers used for identifying mesenchymal stem cells mostly refer to the standards published by ISCT: the cells must express CD73, CD90 and CD105 but do not express CD14, CD34, CD45 and HLA-DR. The combination of biomarkers is based on bone marrow mesenchymal stem cells, but the lack of tissue specificity makes the identification difficult to distinguish mesenchymal stem cells from different tissues. On the other hand, many reports pointed out that the behavior of mesenchymal stem cells from different sources is different. Therefore, it is necessary to develop specific biomolecular markers that distinguish mesenchymal stem cells from specific tissues.

Since a variety of angiogenesis factors expressed in mesenchymal stem cells, mesenchymal stem cells are applied to promote angiogenesis to treat ischemic diseases. However, the mechanism of mesenchymal stem cells from different sources in promoting angiogenesis may be different due to the different performance of their key factors.

SUMMARY OF THE INVENTION

The present invention provides a method for culturing decidual placental mesenchymal stem cells (pcMSCs) having an increased expression level of decoy receptor 3 (DcR3), comprising: culturing the pcMSCs in a culture dish containing a serum-free medium until the pcMSCs adhere to the culture dish; adding at least one inflammatory cytokine to the culture dish containing a serum-free medium, wherein the at least one inflammatory cytokine is Tumor Necrosis Factor-α (TNF-α), Interferon-γ (IFN-γ), or a combination thereof; allowing the at least one inflammatory cytokine to stimulate expression of DcR3 in the pcMSCs for 48 hours; and obtaining the pcMSCs having an increased expression level of DcR3, wherein the increased expression level of DcR3 is significantly higher than that of pcMSCs cultured without the stimulation of the at least one inflammatory cytokine, and P value <0.05.

Decidual placental mesenchymal stem cells (pcMSCs) having an increased expression level of DcR3 obtained by the said culture method is also provided in the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
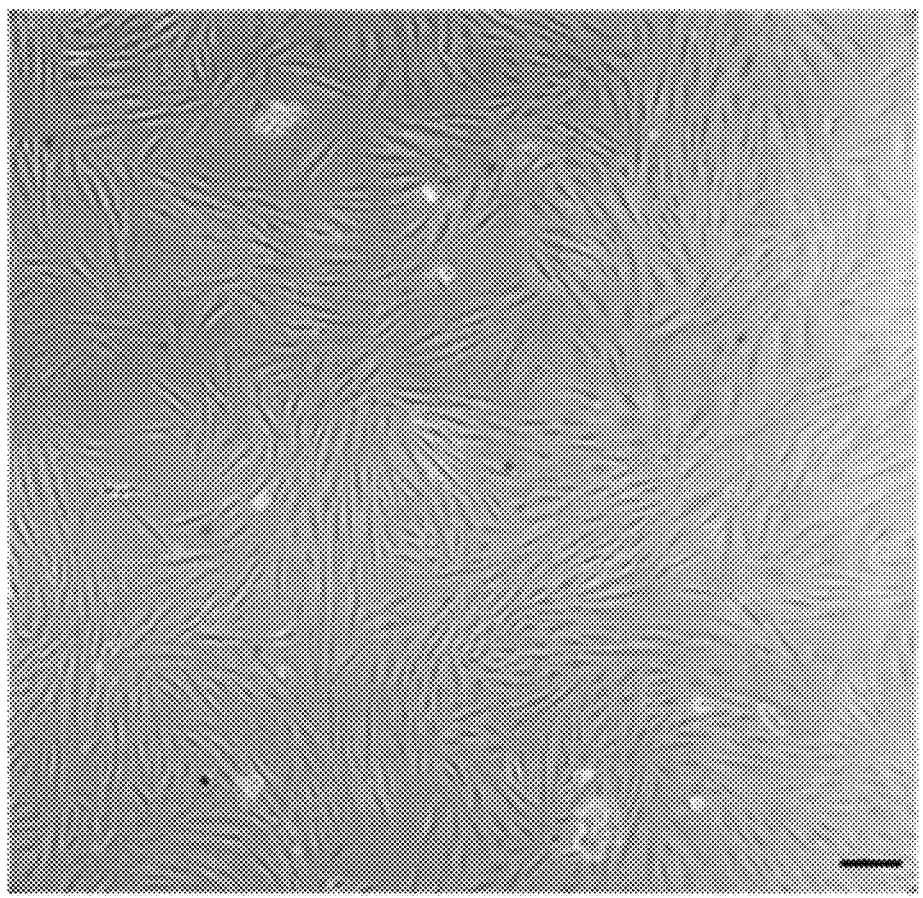
FIG. 1 shows the characterization of decidual placental mesenchymal stem cells (pcMSCs). The morphology of the pcMSCs in serum free culture condition displayed spindle shape adherent cells. Scale bars: 100 μm (FIG. 1A). Immunophenotype analysis of the pcMSCs showed CD29, CD44, CD73, CD90, CD105 positive and CD14, CD34, CD45 and HLA-DR negative (FIG. 1B). In vitro differentiation abilities of the pcMSCs in osteogenesis (2), chondrogenesis (4) and adipogenesis (6) respectively. 1, 3 and 5 representing control group of each in vitro induction condition belonged to osteogenesis, chondrogenesis and adipogenesis respectively. Scale bars: 200 μm (FIG. 1C).

The present invention provides a method for culturing a decidual placental mesenchymal stem cells (pcMSCs) with highly expression of decoy receptor 3 (DcR3), which involves adding an induction step to a serum-free medium formula comprising MCDB201 culture medium, EGF (epidermal growth factor), and ITS (Insulin, Transferrin, Selenium) cell culture supplements, wherein the said induction step is adding at least one inflammatory cytokine to a cell culture medium for stimulation during the process of culturing, so that the decidual placental mesenchymal stem cells (pcMSCs) highly express DcR3.

The term "highly express" or "high expression" of the invention means that the DcR3 expression level of the decidual placental mesenchymal stem cells (pcMSCs) cultured by the culture method of the present invention shows statistically significantly higher than that of decidual placental mesenchymal stem cells (pcMSCs) cultured by the currently existing mesenchymal stem cell culture method.

In the method of the present invention, preferably, the at least one inflammatory cytokine is selected from tumor necrosis factor-α (TNF-α), interferon-γ (IFN-γ) or the combination thereof.

In the method of the present invention, preferably, the induction step is performed after the decidual placental mesenchymal stem cells (pcMSCs) adhered to the culture dish.

In the method of the present invention, most preferably, the effective amount of TNF-α is 15~20 ng/ml, and the effective amount of IFN-γ is 10~20 ng/ml.

In the method of the present invention, most preferably, the decidual placental mesenchymal stem cells (pcMSCs) are stimulated by TNF-α and IFN-γ for 48 hours.

In the method of the present invention, most preferably, the TNF-α and the IFN-γ are added into the cell culture medium together.

A decidual placental mesenchymal stem cell cultured by the said culture method is also provided in the present invention, wherein the decidual placental mesenchymal stem cells (pcMSCs) highly expresses DcR3.

Preferably, the decidual placental mesenchymal stem cells (pcMSCs) express estrogen receptor (ER), progesterone receptor (PR) and DcR3.

To further investigate the applied potential of DcR3 in the decidual placental mesenchymal stem cells (pcMSCs), the present invention also includes a method for promoting angiogenesis in a subject in need thereof, comprising administering an effective amount of the decidual placental mesenchymal stem cells (pcMSCs) to the subject.

Preferably, in the method of the present invention, the subject is human or mammalian.

Preferably, in the method of the present invention, the effective amount of decidual placental mesenchymal stem cells (pcMSCs) is $1 \times 10^4$ cells to $2 \times 10^5$ cells.

DESCRIPTION OF EMBODIMENTS

It should be understood that the detailed description of the embodiments is to illustrate the preferred embodiments of the present invention, and is not intended to limit the present invention to certain embodiments. It should be noted that the present invention is intended to cover all alternative embodiments within the same spirit and scope of the present invention. Some non-essential modifications and adjustments made by others based on the concept of the present invention still belong to the protection scope of the present invention.

Identification of Decidual Placental Mesenchymal Stem Cells (pcMSCs)

In the research of the present invention, we successfully isolated a kind of mesenchymal stem cells from human placental decidua, named decidual placental mesenchymal stem cells (pcMSCs).

Figure 1B:
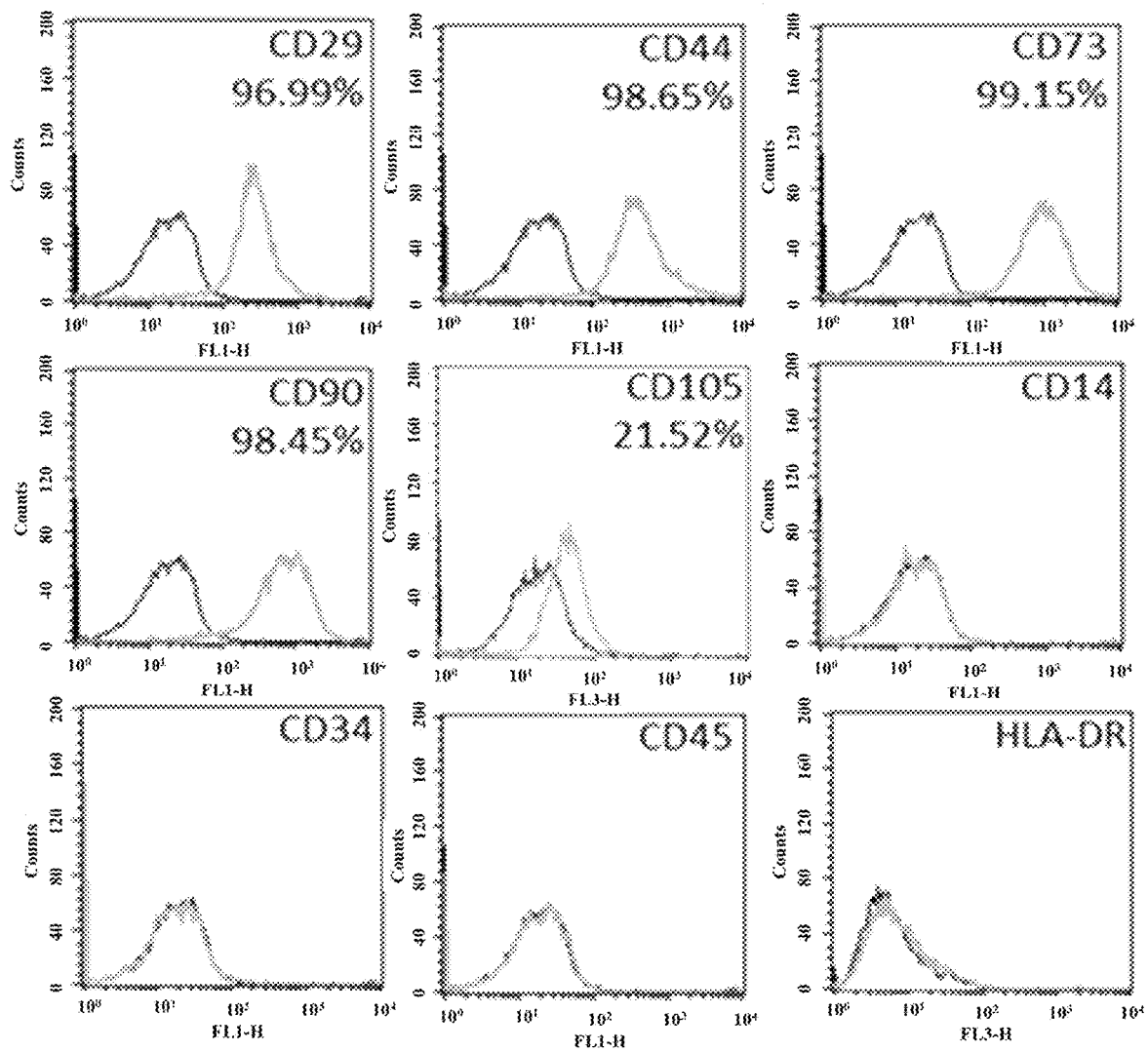
Figure 1C:
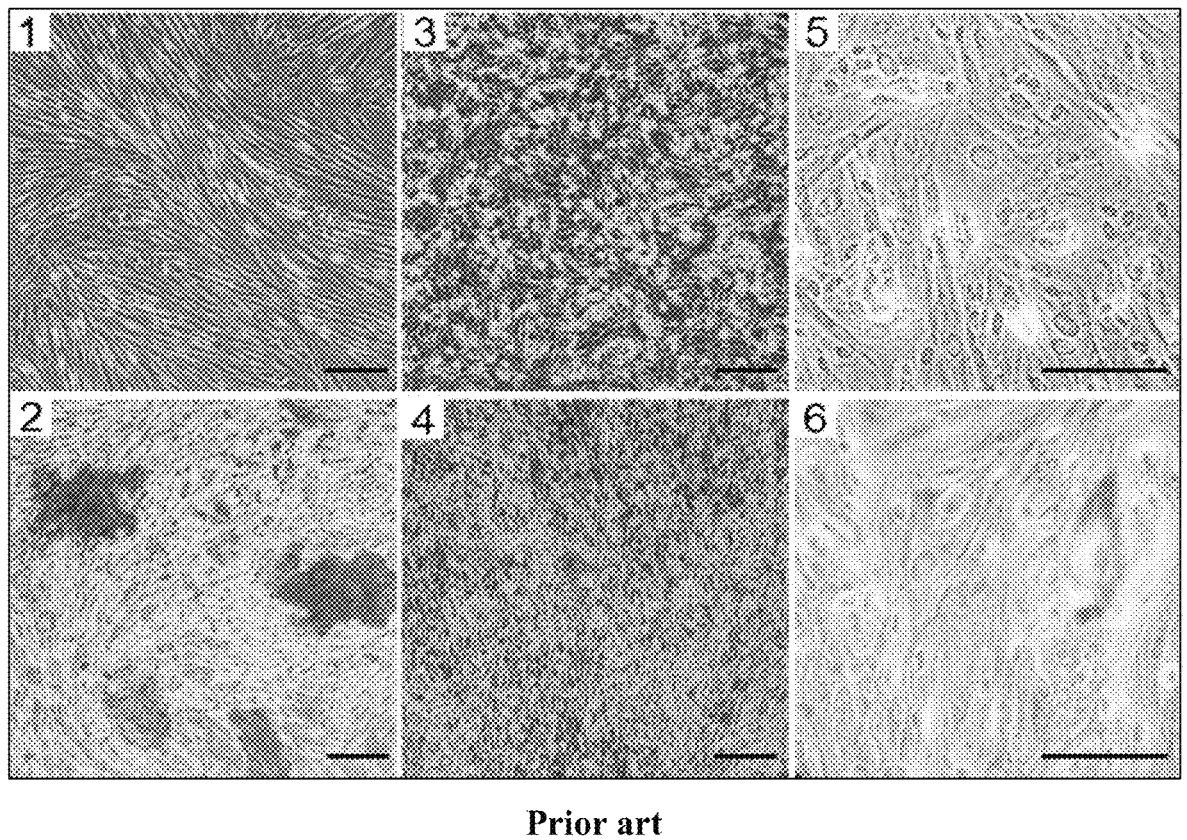
Figure 2A:
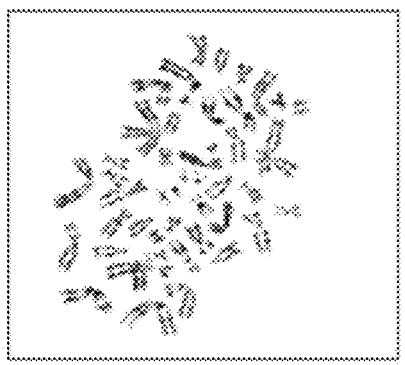
FIG. 2 demonstrates the karyotype of decidual placental mesenchymal stem cells (pcMSCs) isolated from male newborn's placenta. Representative image of chromosome analysis of $20^{th}$ passage the pcMSCs (N100) (FIG. 2A). The analysis presented as 46 separate chromosomes of three individuals including N98 (FIG. 2B), N99 (FIG. 2C), and N100 (FIG. 2D). Fluorescence in situ hybridization of the pcMSCs isolated from male newborn's placenta showed X chromosome (represented as red fluorescence) positive but Y chromosome (represented as green fluorescence) negative (FIG. 2F), in contrast to that in Human umbilical vein endothelial cell (HUVEC) from male newborn presenting double positive result of X and Y chromosomes (FIG. 2E). Given at the left-bottom corners are the enlarged views of the images in white boxes of the individual panels. Scale bars: 50 μm.
Figure 2B:
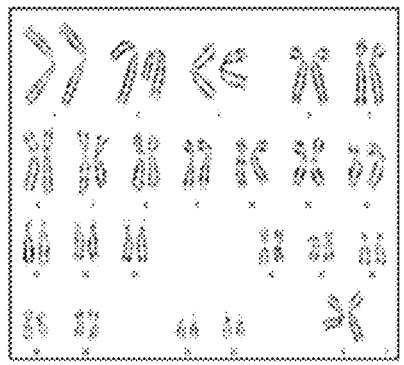
Figure 2C:
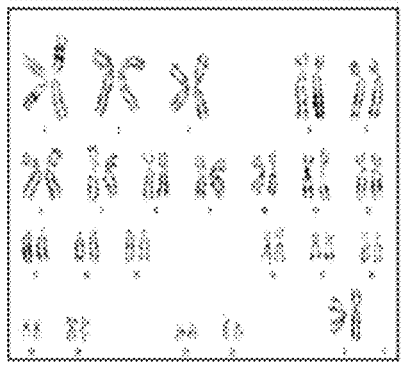
Figure 2D:
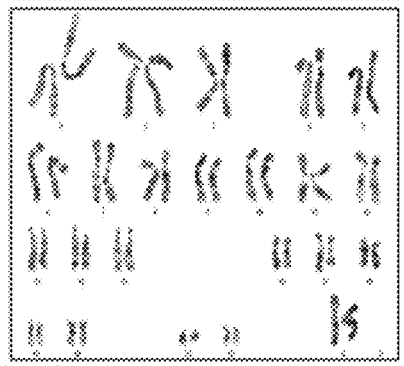
Figure 2E:
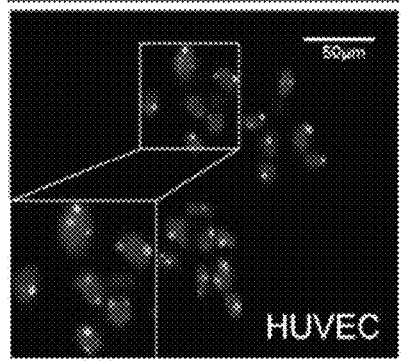
Figure 2F:
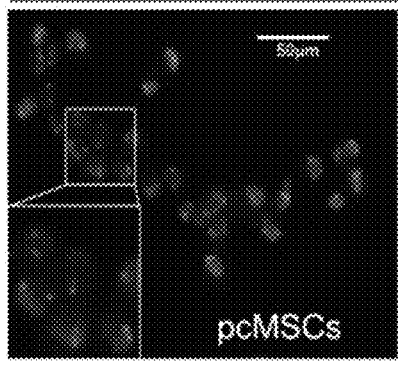

We isolated a mesenchymal stem cell from the decidual part of the placenta, which meet the basic international definition of mesenchymal stem cells (see FIG. 1), and then the cells were confirmed to originate from the maternal site (which is the decidual site) by chromosome identification and fluorescence in situ heterozygous staining analysis (see FIG. 2).

Since the basic definition of mesenchymal stem cells could not distinguish cells separated from different tissue sources, in order to find a biomarker sufficient to identify decidual placental mesenchymal stem cells, the gene expression of bone marrow mesenchymal stem cells and decidual placental mesenchymal stem cells were analyzed in the present invention.

Figure 3:
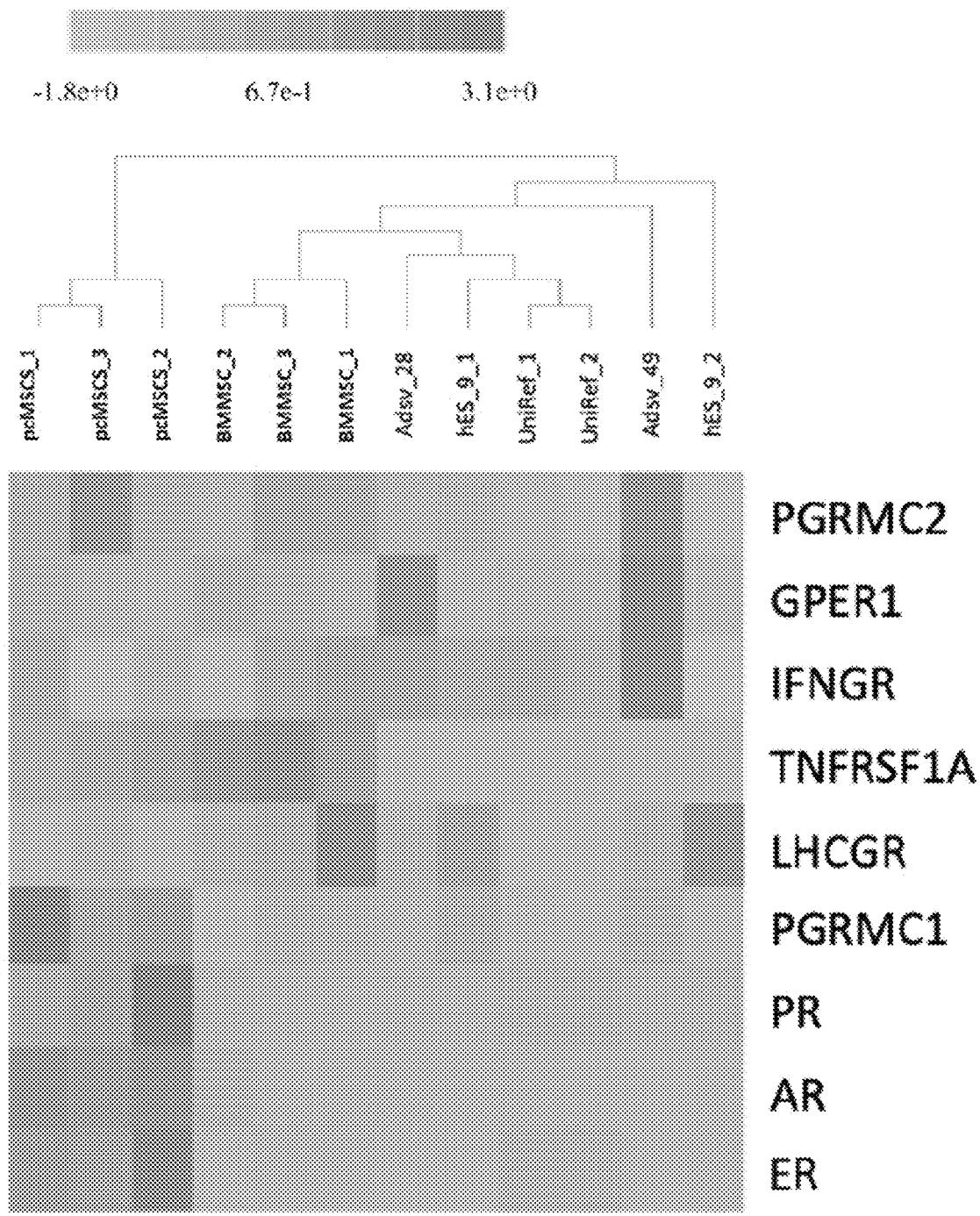
FIG. 3 demonstrates the gene expression analysis of decidual placental mesenchymal stem cells (pcMSCs) comparing to Bone marrow mesenchymal stem cells (BMMSC). Abbreviation: pcMSCs: decidual placental mesenchymal stem cells; BMMSC: bone marrow mesenchymal stem cells; Adsv: adipose mesenchymal stem cells; hES: human embryonic stem cells; UniRef: UniProt Reference Clusters.

Several receptor genes were collected in the present invention to prove the difference between bone marrow mesenchymal stem cells (BMMSCs) and the pcMSCs. As shown in FIG. 3, estrogen receptor (ER) and progesterone receptor (PR) could be expressed in the pcMSCs, but could not be expressed in BMMSCs, and both BMMSCs and the pcMSCs expressed IFN-γ receptor (IFNGR) and TNF-α receptor (TNFRSF1A). The result confirmed that ER and PR were unique to decidual placental mesenchymal stem cells.

Figure 4:
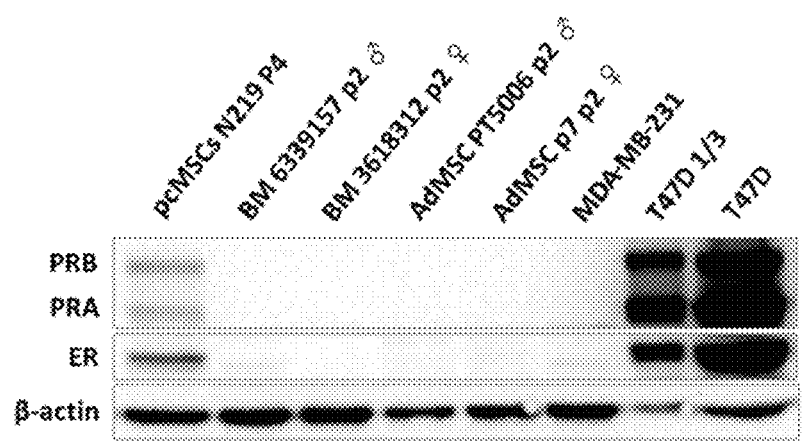
FIG. 4 shows hormone receptors of decidual placental mesenchymal stem cells (pcMSCs) comparing to those of BMMSCs. Abbreviation: BM: bone marrow mesenchymal stem cells; AdMSC: adipose mesenchymal stem cells; PRA: progesterone receptor A; PRB: progesterone receptor B; ER: estrogen receptor α subunit.

Further compared the hormone receptors of the pcMSCs with those of BMMSC, the protein expression was confirmed by different receptor specific antibodies through Western blot, and the breast cancer cell lines MDA-MB-231 and T47D were used as negative and positive controls of progesterone receptor (PR) and estrogen receptor (ER), respectively. The result demonstrated that, after compared to BMMSCs and AdMSCs, only the pcMSCs expressed progesterone receptor (PR) and estrogen receptor (ER) (see FIG. 4).

In order to identify that estrogen receptor and progesterone receptor were unique to decidual placental mesenchymal stem cells, the decidual placental mesenchymal stem cells (pcMSCs) and bone marrow mesenchymal stem cells (BMMSCs) were further stimulated with 10 nM estrogen and 1 μM progesterone (E/P), and the cultured medium and the cells were harvested on day 3, 6 and 9 for subsequently quantitative PCR, Western blotting and ELISA analysis to evaluate the expression of prolactin (PRL). β-actin was used as quantitative standards in Western blotting, all experiments were repeated in triplicate.

Figure 5A:
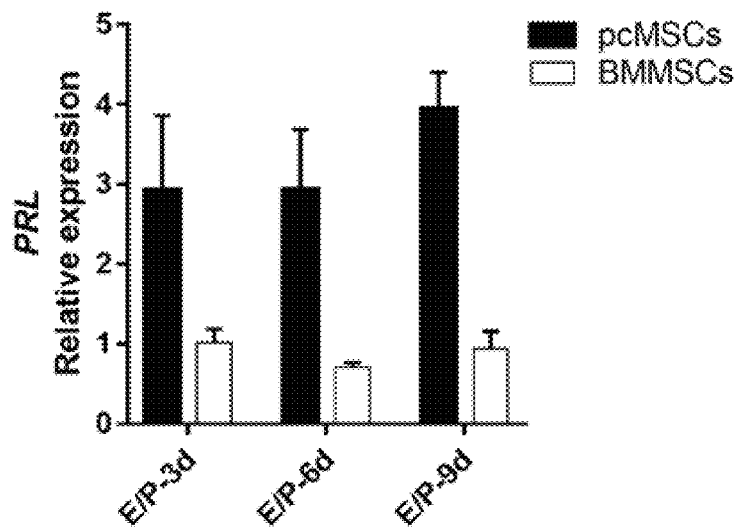
FIG. 5 indicates that decidual placental mesenchymal stem cells (pcMSCs) can be induced in vitro decidualization by estradiol and progesterone. The result of quantitative PCR analysis (FIG. 5A). The result of western blotting (FIG. 5B). The result of ELISA (FIG. 5C). * indicated $0.01<P\leq0.05$,  indicated $0.005<P\leq0.01$, * indicated $P\leq0.005$; and N.D. indicated non-detected.
Figure 5B:
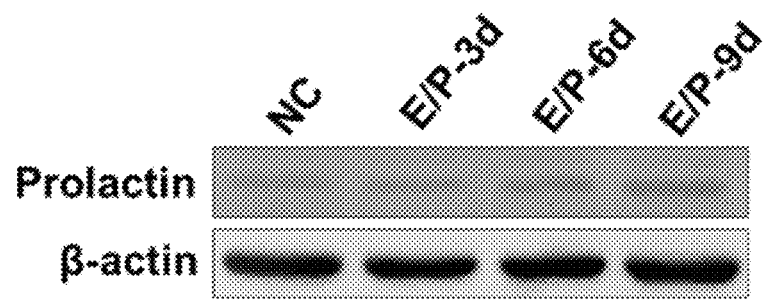
Figure 5C:
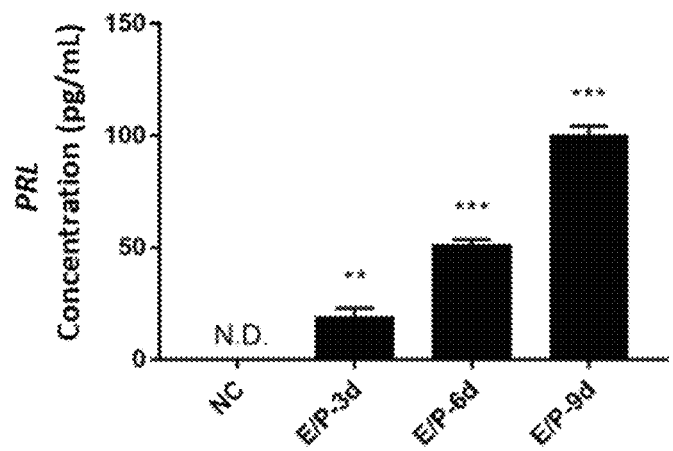

The results were shown as FIG. 5. All the results of qPCR (A), Western blotting (B) and ELISA (C) quantitative analysis demonstrated that the index gene PRL rose significantly in the pcMSCs which indicated that only the pcMSCs could be differentiated into decidualization. The BMMSCs were not regulated by hormones. The results confirmed once again that decidual placental mesenchymal stem cells exhibited their unique behaviors derived from the decidual site.

Moreover, the expression levels of tumor necrosis factor (TNF) receptor superfamily related genes of the pcMSCs and BMMSCs were also compared. The tumor necrosis factor (TNF) receptor superfamily related genes were collected and analyzed to evaluate the specific gene expression patterns between the pcMSCs and BMMSCs.

Figure 6:
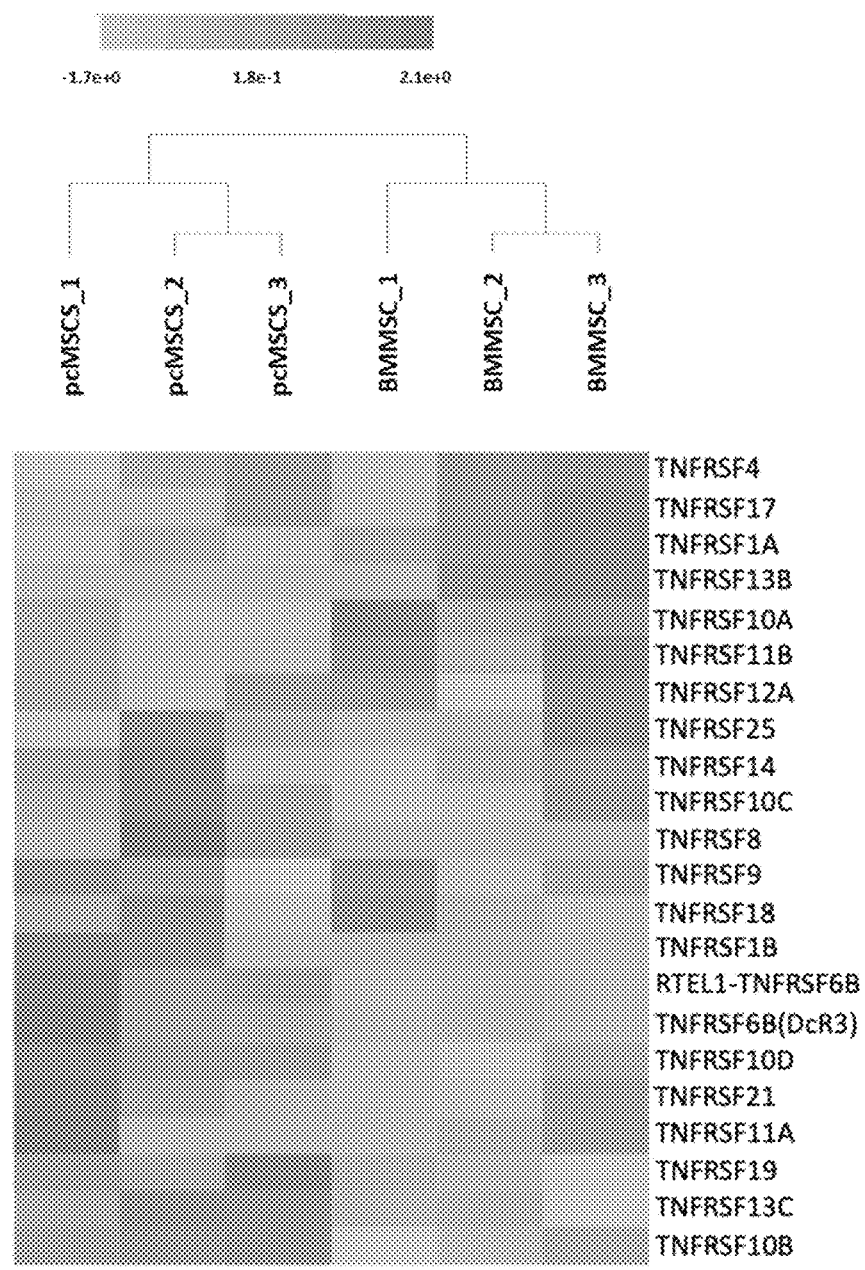
FIG. 6 indicates the comparison of TNF receptor super family associated genes expression of decidual placental mesenchymal stem cells (pcMSCs) and BMMSCs.
Figure 7:
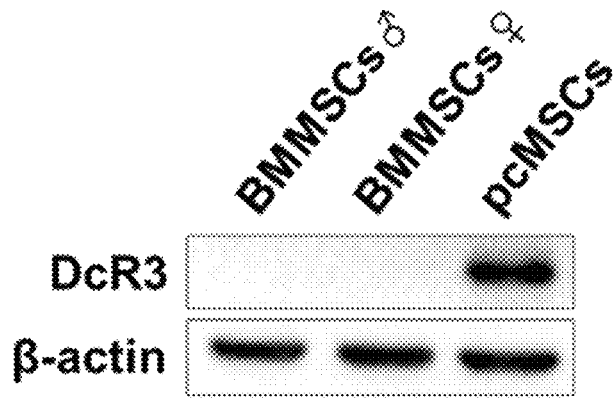
FIG. 7 demonstrates the result of protein expression of DcR3 in decidual placental mesenchymal stem cells (pcMSCs) and BMMSCs.

Although several genes showed distinguishable patterns in the pcMSCs (see FIG. 6), but the decoy receptor No. 3 (DcR3; or TNFRSF6B) was more focused for the further analysis to confirm that DcR3 was expressed only in the pcMSCs but not in BMMSCs. As shown in FIG. 7, the DcR3 was expressed in the pcMSCs but was not expressed in BMMSCs isolated from different genders. Given the above, it was believed that estrogen receptor (ER), progesterone receptor (PR), and decoy receptor type 3 (DcR3) could become physiologically significant biomarkers of the pcMSCs to be used to distinguish the mesenchymal stem cell from different tissues.

Method for Culturing Decidual Placental Mesenchymal Stem Cells (pcMSCs) with Highly Expression of DcR3

The present invention provided a new method for culturing human decidual placental mesenchymal stem cell (pcMSCs) which was adding inflammatory cytokines TNF-α and IFN-γ into a serum-free stem cell culture medium for stimulating the expression of DcR3. In detail, the pcMSCs were cultured by the conventional sterilized cell culture method with using serum-free stem cell culture medium for cell subculture, the fresh stem cell culture medium was renewed every 3 days during the culturing, wherein the medium including MCDB201 culture medium, 1% ITS (Insulin, Transferrin, Selenium) and 10 ng/mL EGF (epidermal growth factor).

Differing from the conventional culturing method, an induction step was added in the present invention after the pcMSCs adhered to the culture dish.

In the present invention, the cells were separated to 4 groups, that were (1) negative control; (2) induction with 20 ng/mL TNF-α; (3) induction with 20 ng/mL IFN-γ; and (4) induction with 20 ng/mL TNF-α and 20 ng/mL IFN-γ together.

Figure 8:
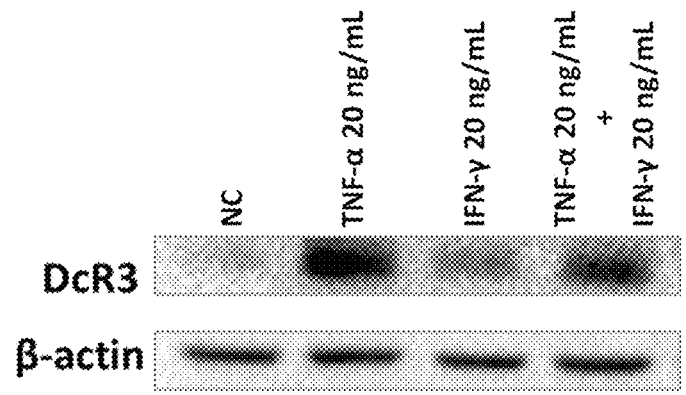
FIG. 8 demonstrates the expression of DcR3 is enhanced by the induction of TNF-α and IFN-γ.

At first, $1\times10^5$ pcMSCs were cultured in 6-well culture plate, culturing overnight in the incubator. The culture medium of each well was removed. Each well was added with group (1) complete medium without stimulated factor, group (2) complete medium with 20 ng/mL TNF-α, group (3) complete medium with 20 ng/mL IFN-γ, and group (4) complete medium having 20 ng/mL TNF-α and 20 ng/mL IFN-γ. The pcMSCs were cultured for 48 hours and then were identified by Western blotting after induction. As shown in FIG. 8, the results indicated that the expression level of DcR3 was increased in induced pcMSCs of groups (2), (3) and (4).

The present invention further tested the applicable dosage of the pcMSCs to increase the expression of DcR3. The result showed that the DcR3 expression of the pcMSCs could be increased by using 15 ng/mL TNF-α or 10 ng/mL IFN-γ. Similarly, when the two cytokines were added together for induction, the result of increasing the expression of DcR3 in the pcMSCs was also observed.

pcMSCs had the Potential to Promote Angiogenesis

To further explore the potential of DcR3 in applications of the pcMSCs, the pcMSCs were used for the research.

The present invention further tested the difference of angiogenesis between the pcMSCs with or without induction with TNF-α and IFN-γ.

Figure 9:
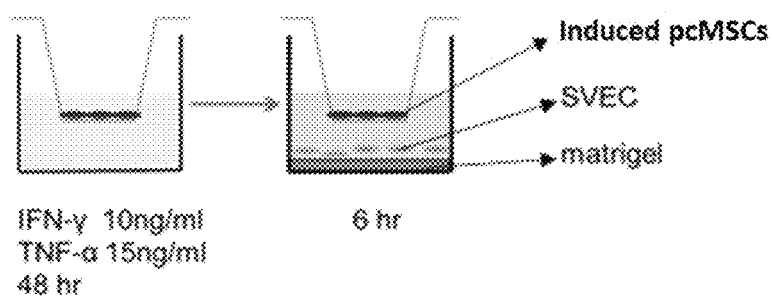
FIG. 9 illustrates that the experiment processes of in vitro tube formation assay demonstrated induced decidual placental mesenchymal stem cells (pcMSCs) promote angiogenesis via DcR3. Abbreviation: SVEC: endothelial cell line.

According to the culturing method described previously, the pcMSCs were cultured in Transwell inserts, the procedures of the experiment were shown in FIG. 9. The used cell number was adjusted according to the pore sizes of the Transwell inserts.

First of all, $1\times10^4$ pcMSCs were cultured in Transwell inserts specific to 24-well culture dish. After induction with 15 ng/mL TNF-α and 10 ng/mL IFN-γ for 48 hours, the Transwell inserts (with induced pcMSCs) were moved to the culture dishes with endothelial cell line (SVEC) for co-culturing to perform the in vitro tube formation assay. The SVECs were cultured on the Matrigel cell culture matrix. The amount of total branch point was calculated with images captured by fluorescence microscopy after 6 hours of co-culture.

Figure 10A:
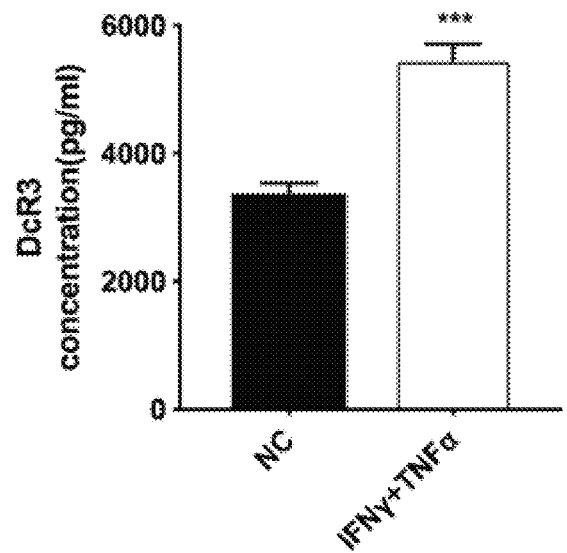
FIG. 10 illustrates that in vitro tube formation assay demonstrated induced decidual placental mesenchymal stem cells (pcMSCs) promote angiogenesis via DcR3. The result of ELISA (FIG. 10A). The fluorescent microscope images (FIG. 10B). The statistical results of fluorescent microscope images (FIG. 10C). * indicated $0.01 < P \leq 0.05$,  indicated $0.005 < P \leq 0.01$, * indicated $P \leq 0.005$.

The DcR3 expression level of the pcMSCs were evaluated by ELISA analysis after induction with cytokines for 48 hours. As shown in FIG. 10A, the DcR3 expression level of induced group was significantly higher than the expression level of non-induced group.

Figure 10B:
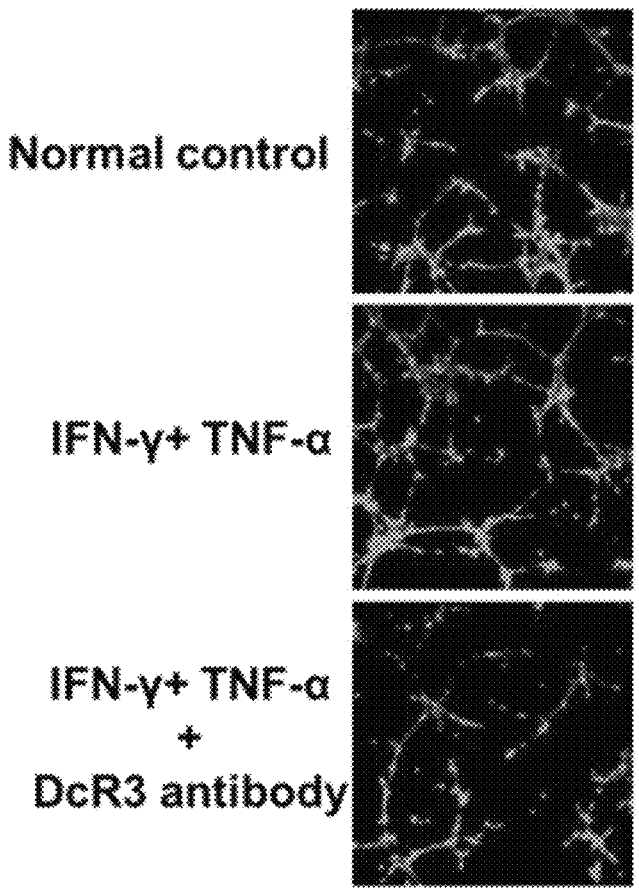

FIG. 10B illustrated the number of total branch points of each group calculated through the images taken by the fluorescence microscope after 6 hours of co-culture of the induced decidual placental mesenchymal stem cells and SVEC.

In the present invention, $2\times10^5$ pcMSCs were also cultured in Transwell inserts specific to 6-well culture dish, and similar results were obtained (data not shown).

Figure 10C:
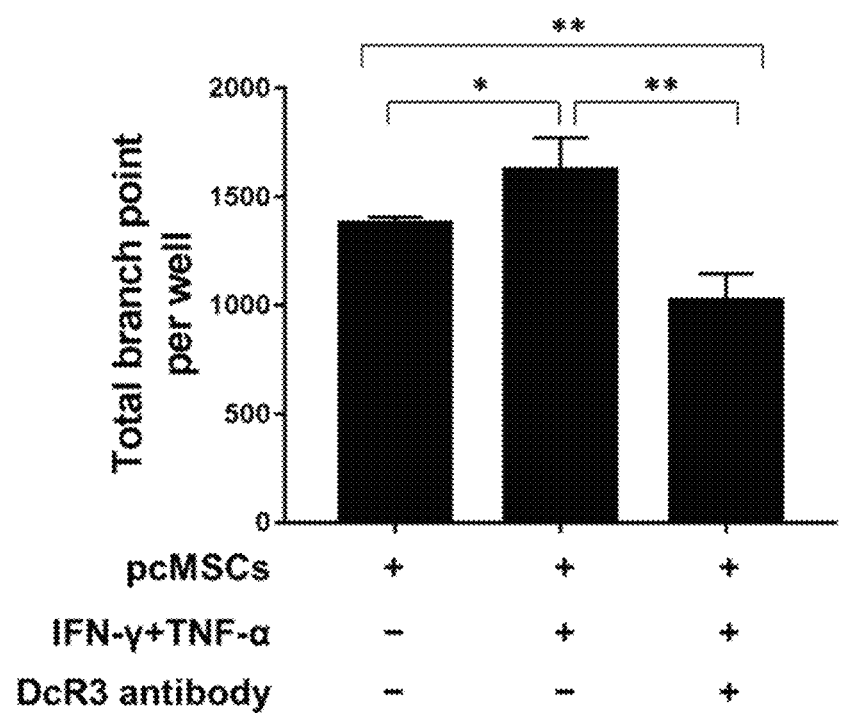

The statistical results showed that, compared with the normal control group, the pcMSCs induced with TNF-α and IFN-γ significantly induced more branch points, and this phenomenon was reversed by anti-DcR3 antibody (0.5 μg/mL) (FIG. 10C). The number of branch points in the neutralization group of the anti-DcR3 antibody showed the lowest, even lower than that of the normal control group. The results reflected that the constant expression of DcR3 had an impact on angiogenesis. Therefore, the pcMSCs could promote angiogenesis by DcR3.

What is claimed is:

1. A method for culturing decidual placental mesenchymal stem cells (pcMSCs) from human to increase the expression level of decoy receptor 3 (DcR3), comprising:
   culturing the pcMSCs from human in a culture dish containing a serum-free medium until the pcMSCs from human adhere to the culture dish;
   adding at least one inflammatory cytokine at an effective amount to the culture dish containing a serum-free medium, wherein the at least one inflammatory cytokine is Tumor Necrosis Factor-α (TNF-α), Interferon-γ (IFN-γ), or a combination thereof;
   allowing the at least one inflammatory cytokine to stimulate expression of DcR3 in the pcMSCs from human for 48 hours; and
   obtaining the pcMSCs from human having increased expression level of DcR3 compared to pcMSCs from human cultured without the stimulation of the at least one inflammatory cytokine, wherein the increase in statistically significant with a P value of less than 0.05.

2. The method of claim 1, wherein the effective amount of TNF-α is 15~20 ng/mL, and wherein the effective amount of IFN-γ is 10~20 ng/mL.

3. The method of claim 1, wherein the TNF-α and the IFN-γ are added into the cell culture medium together.

4. Decidual placental mesenchymal stem cells (pcMSCs) from human having an increased expression level of decoy receptor 3 (DcR3), wherein the pcMSCs from human having an increased expression level of DcR3 are obtained by the method of claim 1.

5. The pcMSCs from human having an increased expression level of DcR3 of claim 4, wherein the said pcMSCs from human having an increased expression level of DcR3 express estrogen receptor (ER), progesterone receptor (PR) and DcR3.

6. The pcMSCs from human having an increased expression level of DcR3 of claim 4, wherein the pcMSCs from human having increased expression level of DcR3 promote angiogenesis as a result of increased expression level of DcR3.

\* \* \* \* \*